United States Patent
Marrero Callicó et al.

(10) Patent No.: US 10,964,018 B2
(45) Date of Patent: Mar. 30, 2021

(54) METHOD OF NON-INVASIVE DETECTION OF TUMOUR AND/OR HEALTHY TISSUE AND HYPERSPECTRAL IMAGING APPARATUS

(71) Applicant: UNIVERSIDAD DE LAS PALMAS DE GRAN CANARIA, Las Palmas de Gran Canaria (ES)

(72) Inventors: Gustavo Marrero Callicó, Las Palmas de Gran Canaria (ES); Himar Antonio Fabelo Gómez, Las Palmas de Gran Canaria (ES); Samuel Ortega Sarmiento, Las Palmas de Gran Canaria (ES); Bogdan Stanciulescu, Paris (FR); Kiran Bangalore Ravi, Paris (FR)

(73) Assignee: UNIVERSIDAD DE LAS PALMAS DE GRAN CANARIA, Las Palmas de Gran Canaria (ES)

( * ) Notice: Subject to any disclaimer, the term of this patent is extended or adjusted under 35 U.S.C. 154(b) by 28 days.

(21) Appl. No.: 16/462,879

(22) PCT Filed: Nov. 22, 2016

(86) PCT No.: PCT/EP2016/078477
§ 371 (c)(1),
(2) Date: May 21, 2019

(87) PCT Pub. No.: WO2018/095516
PCT Pub. Date: May 31, 2018

(65) Prior Publication Data
US 2019/0279362 A1    Sep. 12, 2019

(51) Int. Cl.
*G06T 7/00* (2017.01)
*G06K 9/00* (2006.01)
(Continued)

(52) U.S. Cl.
CPC .............. *G06T 7/0012* (2013.01); *G06K 9/00* (2013.01); *G06K 9/6223* (2013.01);
(Continued)

(58) Field of Classification Search
CPC .............. G02B 27/0172; G02B 27/017; G02B 2027/0187; G02B 2027/0138;
(Continued)

(56) References Cited

U.S. PATENT DOCUMENTS

| | | | |
|---|---|---|---|
| 2017/0367580 A1* | 12/2017 | DiMaio | A61B 5/445 |
| 2020/0134820 A1* | 4/2020 | Hendriks | G06T 7/0012 |

(Continued)

FOREIGN PATENT DOCUMENTS

| | | |
|---|---|---|
| JP | 2012005512 A | 1/2012 |
| WO | WO 2014/118674 A2 | 8/2014 |

(Continued)

OTHER PUBLICATIONS

International Search Report and Written Opinion dated Oct. 10, 2017 for PCT Application No. PCT/EP2016/078477, 23 pages.
(Continued)

*Primary Examiner* — Diane D Mizrahi
(74) *Attorney, Agent, or Firm* — Squire Patton Boggs (US) LLP

(57) ABSTRACT

A method of non-invasive detection of tumor and/or healthy tissue using hyperspectral imaging is provided. The method includes determining a pixel-wise classification of a hyperspectral image obtained from a target tissue by implementing a machine learning approach fed with hyperspectral data of at least one pixel. The method further includes performing a segmentation of the hyperspectral image by grouping pixels into at least one cluster based on the hyperspectral data of each pixel. The same classification is assigned to all
(Continued)

the pixels belonging to the same cluster, so that each cluster is associated with a certain classification.

19 Claims, 2 Drawing Sheets

(51) Int. Cl.
*G06K 9/62* (2006.01)
*G16H 30/40* (2018.01)
*G06K 9/46* (2006.01)

(52) U.S. Cl.
CPC ... *G06K 9/6276* (2013.01); *G06K 2009/4657* (2013.01); *G06K 2209/05* (2013.01); *G06T 2207/10056* (2013.01); *G06T 2207/20081* (2013.01); *G06T 2207/30016* (2013.01); *G06T 2207/30096* (2013.01); *G16H 30/40* (2018.01)

(58) Field of Classification Search
CPC . G02B 2027/0178; G06F 1/163; G06F 3/013; G06T 7/0012; G06T 2207/10056; G06T 2207/20081; G06T 2207/30016; G06T 2207/30096; G06K 9/6276; G06K 9/6223; G06K 9/00; G06K 2209/05; G06K 2009/4657; G16H 30/40
See application file for complete search history.

(56) References Cited

U.S. PATENT DOCUMENTS

2020/0138360 A1* 5/2020 Fan ..................... A61B 5/7264
2020/0272864 A1* 8/2020 Faust ................... G06T 7/0012

FOREIGN PATENT DOCUMENTS

| WO | WO 2014/139020 A1 | 9/2014 |
| WO | WO 2015/023990 A1 | 2/2015 |
| WO | WO2015/162694 A1 | 10/2015 |

OTHER PUBLICATIONS

Boas, et al: "Chapter 7. Multi/Hyper-Spectral Imaging", Jan. 1, 2011 Handbook of Biomedical OP, CRC Press, USA, pp. 131-163, XP009194453, ISBN: 978-1-4200-9036-9 p. 152-p. 153; figure 7.15.

Christophe, et al: "Comparison and evaluation of quality criteria for hyperspectral imagery", Proceedings vol. 9025 IS&T/SPIE Electronic Imaging: Feb. 2-6, 2014; Intelligent Robots and Computer Vision XXXI: Algorithms and Techniques, vol. 5668, Jan. 17, 2005, p. 204, XP055410024. US ISSN: 0277-786X, DOI: 10.1117/12.587107 ISBN: 978-1-5106-1354-6, p. 209.

Fabelo, et al: "A Novel Use of Hyperspectral Images for Human Brain Cancer Detection using in-Vivo Samples", Proceedings of the 9th International Joint Conference on Biomedical Engineering Systems ANO Technologies, Jan. 1, 2016, pp. 311-320, XP055394151, DOI: 10.5220/0005849803110320 ISBN: 978-989-7581-70-0 p. 314-p.0316; figure 6.

Lu, et al: "Spectral-spatial classification for noninvasive cancer detection using hyperspectral imaging", International Society for Optical Engineering, SPIE, PO Box 10 Bellingham WA 98227-0010 USA, vol. 19, No. 10, Oct. 1, 2014, p. 106004, XP060047120, ISSN: 1083-3668, DOI: 10.1117/1.JBO.19.10.106004 [retrieved on Oct. 2, 2014] p. 3 pp. 4, 6.

Pike, et al: "A minimum spanning forest based hyperspectral image classification method for cancerous tissue detection", Progress in Biomedical Optics and Imaging, SPIE—International Society for Optical Engineering, Bellingham. WA, US, vol. 9634, Mar. 21, 2014, pp. 90341W-90341W, XP060031740, ISSN: 1605-7422, DOI: 10.1117/12.2043848 ISBN: 978-1-5106-0027-0, p. 4; figure 1.

Su, et al: "A filter-based post-processing technique for improving homogeneity of pixel-wise classification data", European Journal of Remote Sensing, vol. 49, No. 1, Sep. 8, 2016, pp. 531-552, XP055394277, DOI: 10.5721/EuJRS20164928, p. 532.

Tarabalka, et al: "Multiple Spectral-Spatial Classification Approach for Hyperspectral Data", IEEE Transactions on Geoscience and Remote Sensing, IEEE Service Center, Piscataway, NJ, US, vol. 48, No. 11, Nov. 1, 2010 (Nov. 1, 2010), pp. 4122-4132, XP011318509, ISSN: 0196-2892 p. 4124-p. 4126; figures 2, 3.

* cited by examiner

METHOD OF NON-INVASIVE DETECTION OF TUMOUR AND/OR HEALTHY TISSUE AND HYPERSPECTRAL IMAGING APPARATUS

The present disclosure relates to a method of non-invasive detection of tumor and/or healthy tissue using hyperspectral imaging and also relates to a hyperspectral imaging apparatus.

BACKGROUND

It is known the use of the hyperspectral imaging for several technical fields such as remote sensing, food quality inspection, drug analysis, defence and security, and medical applications.

The hyperspectral imaging is used in various medical applications particularly for differentiation between organs and for identification of tissues e.g. healthy, malignant, etc. One of the most promising implementations relates to the identification of brain cancer.

Brain cancer is one of the most important forms of the disease, and is a significant economic and social burden across Europe. The most common form is high-grade malignant glioma, which accounts for approximately 30-50% of primary brain cancers, with multiform glioblastoma making up 85% of these cases. These types of gliomas are characterized by fast-growing invasiveness, which is locally very aggressive, are in most cases unicentric and are rarely metastasizing.

Despite the introduction of new aggressive treatments combining surgery, radiotherapy and chemotherapy, there continues to be treatment failure in the form of persistent or locally recurrent tumours (i.e. recurrence at the primary tumor location or within 2-3 cm of adjacent tissue). Median survival periods and 5-year survival rates for anaplastic astrocytomas are only 36 months and 18% respectively, whereas for glioblastoma multiforme these are 10 months and less than 5%, respectively.

The relevance and importance of complete resection for low grade tumours is well known, especially in pediatric cases. However, traditional diagnoses of internal tumours are based on excisional biopsy followed by histology or cytology. The main weakness of this standard methodology is twofold: firstly, it is an aggressive and invasive diagnosis with potential side effects and complications due to the surgical resection of both malign and healthy tissues; and secondly, diagnostic information is not available in real time and requires that the tissues are processed in a laboratory.

There are several alternatives to conventional optical visualisation through a surgical microscope, including magnetic resonance imaging (MRI), computed tomography (CT), ultrasonography, Doppler scanning and nuclear medicine. Unlike these approaches, hyperspectral imaging offers the prospect of precise detection of the edges of the malignant tissues in real time during the surgical procedure in a non-invasive and non-ionized way.

WO2015023990A1 discloses an imaging system based on fluorescence imaging. The system is configured to display hyperspectral images taken under stimulus light as fluorescent images, and corrected for optical properties of tissue to provide quantitative maps of fluorophore concentration. Spectral information from hyperspectral images is processed to provide depth of fluorophore below the tissue surface. Quantitative images of fluorescence at depth are also prepared. The system does not provide qualitative maps displaying the different components of the image as the precise tumor localization or the normal tissue.

WO2014139020A1 is related to systems, methods and devices which apply hyperspectral imaging to illuminated brain tissues during invasive port based surgical procedures. This system is not focused in the brain cancer detection and does not perform a classification to identify the different materials found during surgery.

WO2014118674A2 discloses a medical hyperspectral imaging system for identifying a target structure using an algorithm fed with hyperspectral data from an optical surface probe. The system needs for the previous probe measurement data of the patient in order to provide reliable output. The output is valid only for the same patient. The system is not general enough to cope with different patient's samples.

SUMMARY

In a first aspect, a method of non-invasive detection of tumor and/or healthy tissue using hyperspectral imaging is disclosed. The method may comprise:
  determining a pixel-wise classification of a hyperspectral image obtained from a target tissue by implementing a machine learning approach fed with hyperspectral data of at least one pixel;
  performing a segmentation of the hyperspectral image by grouping pixels into at least one cluster based on the hyperspectral data of each pixel;
  assigning the same classification to all the pixels belonging to the same cluster, so that each cluster may be associated with a certain classification.

The method allows providing the skilled person with the highly accurate location and the borders of the different target tissues, materials and substances. The target tissues, materials and substances may be identified avoiding aggressive and invasive diagnosis (no drugs, substances or radiation need to be applied neither invasive ports) with potential side effects and complications due to the surgical resection of both malign and healthy tissues; and diagnostic information may be available in real time and does not require that the tissues are processed in a laboratory.

The method may also help to confirm complete resection, avoid accidental leave of malignant tissue, avoid complications due to "brain mass shift", avoid misalignment between MRI (magnetic resonance imaging) and real brain position, as the state-of-the-art implementations do.

It has been found that the combination of the pixel-wise classification and the segmentation of the hyperspectral image may provide some effects. On the one hand, the segmentation obtained show good capability in finding homogeneous data structures (e.g. clusters) and their boundaries from a hyperspectral cube, and on the other hand the pixel-wise classification may provide robust information regarding the tissue, material or substance which may be assigned to the cluster. Such combination may allow an accurate and useful differentiation between benign and malignant tumours, which may have an extremely proximal spectrum.

The term "cluster" should be understood as a synonym of region or any defined group of pixels or area.

In some examples, the method may further comprise:
  performing a spatial homogenization of the pixel-wise classification, prior to assigning the same classification for all the pixels belonging to the same cluster. It has been found that by homogenizing the pixel-wise classification the output of the method may have an even more accurate location and extension of the target tissues.

In other examples, the method may further comprise:

training the machine learning approach with ground-truth labelled dataset. The method may not need for a previous probe measurement data of the patient in order to provide reliable output. The output may be valid for more than one patient (different people), and one type of tissue.

In examples of the method, the ground-truth labelled dataset may be obtained by:

selecting at least one reference pixel in a hyperspectral image to be labelled;

computing a spectral angle of each pixel with respect to the reference pixel;

generating a spectral angle map (or any other visual representation) which may take into account a predetermined spectral angle threshold related to the reference pixel;

assigning a label to a region (or zone) of the hyperspectral image which may comprise pixels with a spectral angle within the predetermined spectral angle threshold;

generating a ground truth map (or any other visual representation) which may comprise the labelled regions; wherein the label may comprise pathological status.

That features generates a robust and efficient ground-truth, since the labels may be assigned taking into account common and proved features of different target tissues, substances, etc.

In another aspect, a hyperspectral imaging apparatus is disclosed. The apparatus may comprise:

an optical device configured to display a visible image of a target tissue;

a camera configured to obtain hyperspectral images of the target tissue;

a processing platform in data communication with the camera and the optical device;

the optical device may be also configured to display information (such as a map) obtained from processed hyperspectral images;

the processing platform may be configured to implement a method according to any of herein disclosed examples of method.

In another aspect, a computer program product is disclosed. The computer program product may comprise program instructions for causing a computing system to perform a method of non-invasive detection of tumor and/or healthy tissue using hyperspectral imaging according to some examples disclosed herein.

The computer program product may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the processes. The carrier may be any entity or device capable of carrying the computer program.

For example, the carrier may comprise a storage medium, such as a ROM, for example a CD ROM or a semiconductor ROM, or a magnetic recording medium, for example a hard disk. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

In another aspect, a computing device is disclosed. The computing device may comprise a memory and a processor, embodying instructions stored in the memory and executable by the processor, the instructions comprising functionality to execute a method of non-invasive detection of tumor and/or healthy tissue using hyperspectral imaging according to some examples disclosed herein.

BRIEF DESCRIPTION OF THE DRAWINGS

Non-limiting examples of the present disclosure will be described in the following, with reference to the appended drawings, in which.

DETAILED DESCRIPTION OF EXAMPLES

Figure 1:
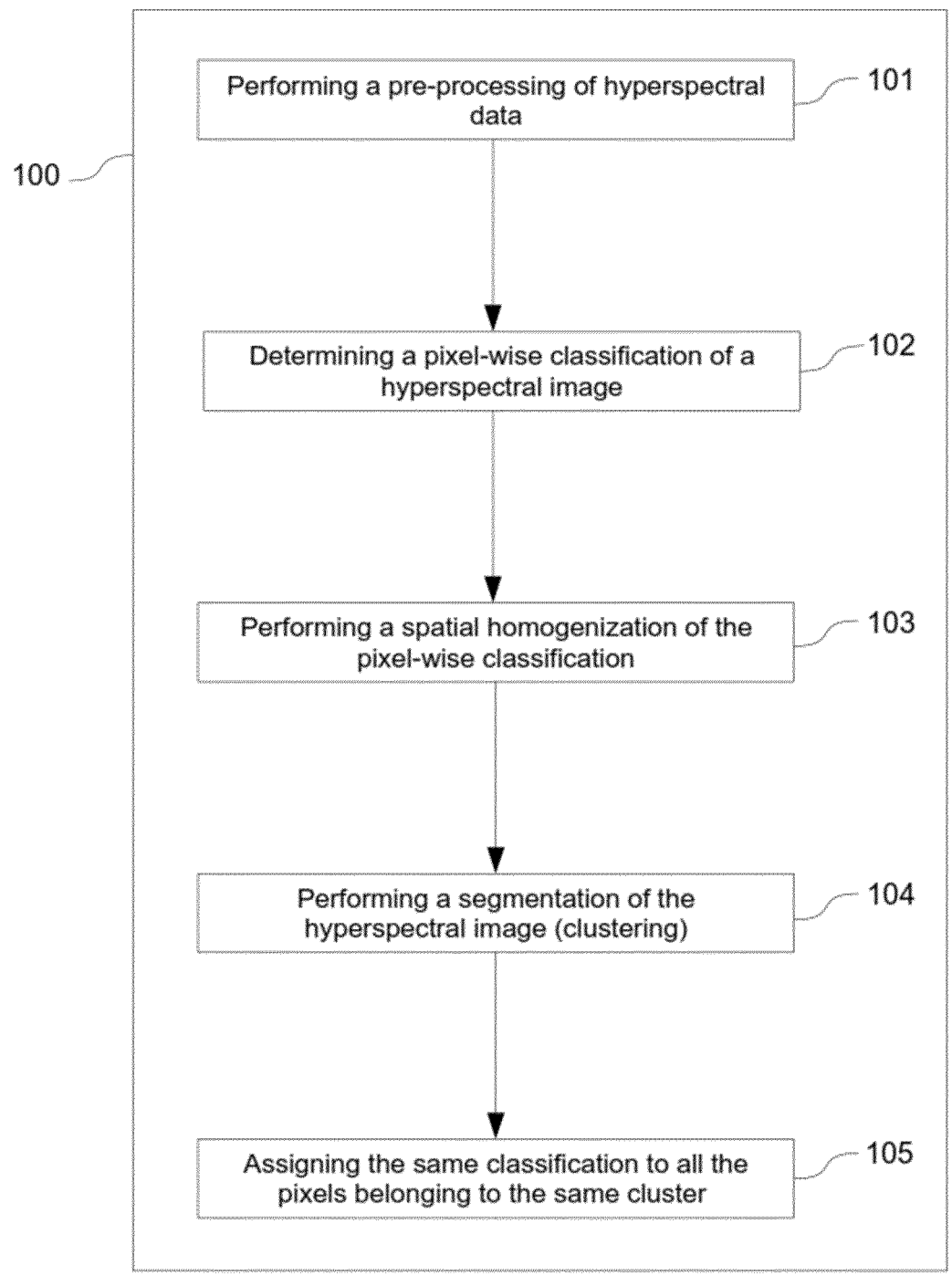
FIG. 1 is a flow chart of a method of non-invasive detection of tumor and/or healthy tissue using hyperspectral imaging according to an example.

FIG. 1 is a flow chart of a method 100 of non-invasive detection of tumor and/or healthy tissue using hyperspectral imaging according to a possible example. Although FIG. 1 shows a specific sequence, it should be understood that other sequences may be followed not deviating from the scope of the present disclosure. The method may comprise determining a pixel-wise classification of a hyperspectral image 102 obtained from a target tissue 5 by implementing a machine learning approach fed with hyperspectral data of at least one pixel of the image. Such machine learning approach may comprise a supervised classifying algorithm. The method may further comprise generating a pixel-wise classification map (or any other visual representation) of the hyperspectral image, after determining the pixel-wise classification.

According to examples, the classification may comprise at least one of the following classes: tumor tissue, healthy tissue, hypervascularized tissue, blood vessel, background element, primary tumor tissue and metastatic tumor tissue. This group of classifications may be enlarged if necessary.

The supervised classifying algorithm may be, for instance, Support Vector Machine (SVM), Artificial Neural Networks (ANNRandom Forest (RF) or Adaboost. However, the skilled person could choose another algorithm depending on the needs.

The method may also comprise performing a segmentation of the hyperspectral image 104 by grouping pixels into at least one cluster based on the hyperspectral data of each pixel. After performing the segmentation of the hyperspectral image, a segmentation map of the hyperspectral image may be generated. Such segmentation of the hyperspectral image may be performed through an unsupervised clustering algorithm.

The unsupervised clustering algorithm may be, for instance, Hierarchical rank-2 NMF (H2NMF), Hierarchical K-means (HKM) or Hierarchical Spherical K-means (HSKM). However, the skilled person could choose another algorithm depending on the needs.

The method may also comprise assigning the same classification to all the pixels belonging to the same cluster 105, so that each cluster may be associated with at least one certain classification. According to some examples, a classification may be assigned to the cluster corresponding to the most frequent pixel classification in each cluster. After assigning the same classification to all the pixels belonging to the same cluster, the method may further comprise generating a cluster-wise classification map of the hyperspectral image.

According to some examples, the method may further comprise assigning in the cluster-wise classification map different chromatic properties to clusters with different classifications to each other. Some predefined chromatic properties may be related to each classification, for example:
- green=normal tissue
- red=tumor tissue
- blue=blood vessels and hypervascularised tissue
- black=background elements and other tissue, materials or substances In some other examples, the method may further comprise degrading chromatic properties of a cluster depending on the probability of the assigned classification. Then a degradation density map may be generated taking into account only the maximum probability results obtained per each cluster. The colour of each class may be degraded using the percentage of the probability. For example, if the probability of tumor class for a certain cluster is 80%, the cluster colour may be degraded a 20% (cluster RGB colour will be Red=0.8, Green=0, Blue=0).

According to some examples, the method may further comprise mixing different chromatic properties related to different classifications in the same cluster. It may take into account the percentage of the probability of different classifications in the cluster. Then a mix density map may be generated which may take into account the three maximum probability values per each cluster. The colour of each class may be mixed using the percentage of the probability of the three maximum values. For example, if the probability of tumor class for a certain cluster is 70%, the probability of the normal tissue is 5% and the probability of the blood vessels is 25%, the cluster RGB colour may be Red=0.7, Green=0.05 and Blue=0.25.

The percentage of probability for each cluster may be obtained through a process such as majority voting which will be described later on.

Prior to assigning the same classification for all the pixels belonging to the same cluster, the method may comprise performing a spatial homogenization of the pixel-wise classification 103. It has been found that the spatial homogenization may help in a further improvement of the spatial coherence of the pixel-wise classification results and then the cluster-wise classification results may be significantly improved.

According to further examples, the method may comprise generating a spatially homogenized pixel-wise classification map of the hyperspectral image, after performing a spatial homogenization of the pixel-wise classification. The spatial homogenization of the pixel-wise classification may comprise:
- performing a dimensionality reduction of the hyperspectral data of each pixel;
- implementing a filtering approach fed with pixel-wise classification data and dimensionally-reduced hyperspectral data; the filtering approach may assign to a pixel the most common classification among its pixel-neighbours.

Dimensionally-reduced hyperspectral data may be obtained from implementation of a band-reducing algorithm, such as a Principal Component Analysis (PCA) algorithm. The skilled person could use other band-reducing algorithms depending on the needs.

According to some examples, the method may comprise performing a pre-processing of the hyperspectral data 101, which may be carried out prior to at least one of: determining the pixel-wise classification 102, performing the segmentation 104, and assigning the same classification 105. The pre-processing of the hyperspectral data may comprise at least one of the following: image calibration, noise filtering and noise removing, band averaging and normalization.

According to further examples, a pre-processing chain may be provided which comprises all or part of the above cited pre-processing processes.

The image calibration may comprise correcting variations in the spectral signature of each pixel which may be caused by non-uniform illumination over a surface of the target tissue 5. An acquired raw image may be calibrated using white and dark reference images previously obtained under the same illumination conditions. A hyperspectral calibrated image may be calculated by comparing the acquired raw image with previous white and dark reference images.

The noise filtering and noise removing may comprise reducing at least a part of spectral noise of the hyperspectral image. This noise may be generated by a CCD sensor and a dispersive element of a hyperspectral camera (e.g. VNIR). For instance, bands from 0 to 55 and from 750 to 826 may be removed since those bands may contain too much noise. Bands may be reduced from 826 to 695 bands which may be those containing useful information about tissues, particularly for discrimination between tumor and healthy tissues as it has been found.

Another possible reason to avoid extreme bands may be that hyperspectral cameras may suffer from poor repeatability index.

The skilled person will be able to vary those band ranges for each case.

Due to an extremely high spectral resolution of the images, consecutive bands may be correlated, providing redundant information which may be removed. The band averaging may comprise removing at least one band of the hyperspectral image; the removed band may be correlated with another consecutive band.

The normalization may comprise homogenizing the amplitude of each pixel without modifying the shape of its spectral signature. This normalization may correct different brightness of each pixel of the image due to captures at different height, and hence, at different radiation intensity.

By implementing the pre-processing, a high level of contrast may be obtained to distinguish for instance between veins, normal tissues and/or tumor tissues. The pre-processing may simplify, reduce, and clean the hyperspectral data.

According to some other examples, the method may comprise training the machine learning approach with ground-truth labelled dataset. A process may be provided for obtaining a ground-truth labelled dataset as follows:
- selecting at least one reference pixel in a hyperspectral image to be labelled;
- computing a spectral angle of each pixel with respect to the reference pixel;
- generating a spectral angle map taking into account a predetermined spectral angle threshold related to the reference pixel;

assigning a label to a region of the hyperspectral image which may comprise pixels with a spectral angle within the predetermined spectral angle threshold;

generating a ground truth map which may comprise the labelled regions;

wherein the label may comprise pathological status.

By obtaining the ground-truth labelled dataset as above described the results obtained by the pixel-wise algorithm may be improved, owing to the robustness of the labelled dataset.

Once trained, the machine learning approach may be validated. A specific validation labelled dataset may be used for that operation. The method may also comprise generating a mathematical classifier model which may be implementable by the machine learning approach. That mathematical classifier model may be trained and even validated as disclosed herein.

According to some examples which allow obtaining the ground-truth labelled dataset, a pixel may be selected by a skilled person from a RGB image to be labelled based on the visual appearance. The RGB image may be of target tissue 5 of a person or different people. Once the reference pixel has been selected, due to the difficulty of assigning a pixel to a certain classification with certain degree of assurance, the spectral angle (SA) between the selected pixel and the other pixels in the hyperspectral cube may be calculated. By applying a predetermined threshold, a binary mask may be obtained. By adjusting this threshold dynamically, a new RGB image may be generated, containing only the pixels for which their spectral angle with respect to the reference pixel may be lower than the threshold. Then, the region of interest may be selected and a label may be assigned to the pixels inside this region. The threshold may be adjusted until the displayed area matches with an expected type of tissue.

This framework for labelling may provide at least two effects. On the one hand, when a reference pixel is selected by a skilled person it may be possible to ensure that the pixels belong to a certain classification by looking at the pixels with the lower SA respect to the reference pixel. On the other hand, a process of manually selecting multiple pixels from a hyperspectral cube for each classification may be a time-consuming task, so this process allows the skilled person collecting some pixels from a given classification with less effort. The skilled person may interact with the framework for labelling if necessary and may vary the ground-truth labelled dataset accordingly. Easy modifications may be envisaged, for instance in case of having new images or if further classifications may be needed to be defined.

According to some examples, the method may comprise sending a control signal from a processing platform/device 4 to a camera 3, such as a hyperspectral camera, for obtaining a hyperspectral image of the target tissue 5, and/or receiving the hyperspectral image of the target tissue 5. The control signal and the hyperspectral image may be sent through a communication network.

Figure 2:
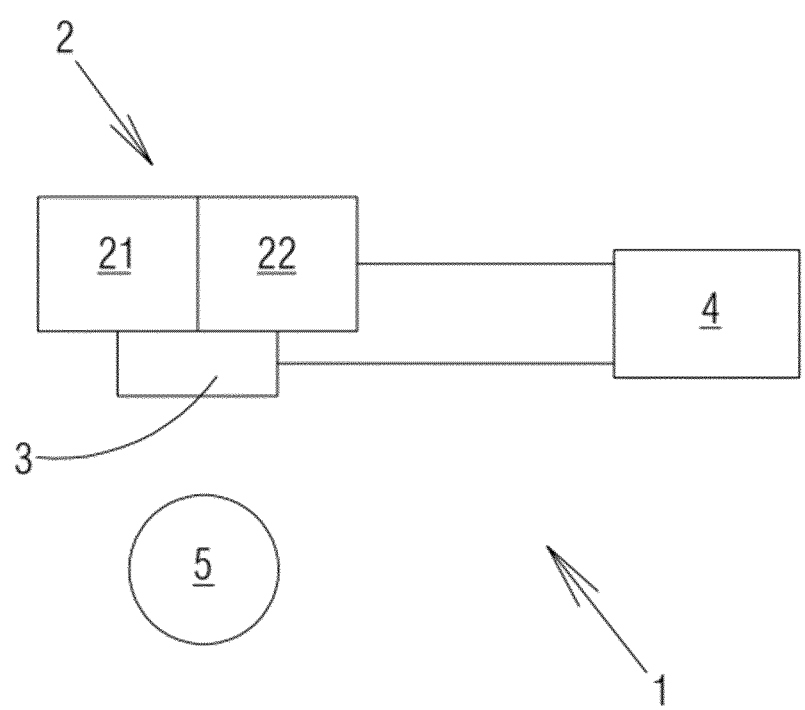
FIG. 2 schematically illustrates a hyperspectral imaging apparatus according to an example.

FIG. 2 schematically illustrates a hyperspectral imaging apparatus 1 according to an example. The hyperspectral imaging apparatus 1 may comprise:

an optical device 2 which may be configured to display a visible image of a target tissue 5;

a camera 3 which may be configured to obtain hyperspectral images of the target tissue 5. In some examples the apparatus may comprise two hyperspectral cameras: NIR and VNIR;

a processing platform 4 in data communication with the camera 3 and the optical device 2;

the optical device 2 may be also configured to display information such as at least a map or any other visual representation obtained from processed hyperspectral images;

the processing platform 4 may be configured to implement a method according to any of the herein discloses examples.

The optical device 2 may comprise a surgical microscope; the surgical microscope may comprise one eyepiece 21 configured to display the visible image of the target tissue 5 and another eyepiece 22 configured to display the information such as at least a map or any other visual representation obtained from processed hyperspectral images.

The camera 3 and the processing platform 4 may be placed in the same or different locations, for instance an operating theatre (not shown). Therefore, a possible implementation of the apparatus 1 may comprise a camera 3 and an optical device 2 in the operating theatre and the processing platform 4 provided apart. In other alternatives, the processing platform 4 may be provided in the same location as camera 3 and optical device 2.

A possible implementation of the method as disclosed herein may comprise the acquisition of a hyperspectral image from a target tissue 5 (such as tissue from brain), for example through the camera 3. The skilled person may select an area of interest of the target tissue 5, for example through the optical device 2. The acquired hyperspectral image may be pre-processed as described above, for example through the processing platform 4. The dimensional reduction approach may use as input a pre-processed hyperspectral cube from each pixel of the image without a band averaging applied since for the dimensional reduction, may be better to use all the information available captured by the sensor of the camera 3. On the other hand, the supervised pixel-wise classification and the unsupervised clustering may employ the hyperspectral cube with the whole pre-processing chain as described herein, but it can be envisaged a supervised pixel-wise classification and/or an unsupervised clustering using a partially pre-processed hyperspectral image, i.e. not all the pre-processing processes or pre-processing chain. It should be pointed out that the band averaging may be applied to VNIR hyperspectral cubes since NIR hyperspectral cubes may not have so much redundant information; the number of bands obtained in this NIR spectral range may be for example 172.

An algorithm may be used to reduce the dimensionality of the hyperspectral images captured as mentioned earlier. That dimension-reducing algorithm may be aimed to spatially homogenizing supervised pixel-wise classification results. The input of the dimension-reducing algorithm may be the pre-processed hyperspectral cube without applying band averaging. A one-band representation of the dimension-reducing algorithm may be obtained and it may be one of the inputs of further filtering algorithms such as the spatial-spectral classification algorithm A supervised pixel-wise classification may be generated, for instance as a map. Supervised classifier algorithm may be trained as above described so as to provide good quantitative and qualitative results. The implementation of the prediction part of this supervised classifier algorithm may be performed on the processing platform 4.

The classification results provided by the pixel-wise classification algorithm and the dimension-reducing algorithm may be used as input of a spatial-spectral classification algorithm (for spatial homogenization of the pixel-wise classification 103). Then, a spatial-spectral supervised classification map or the like may be generated.

The spatial-spectral classification algorithm may be, for instance, K-Nearest Neighbours (KNN) filtering process or any other algorithm suitable for filtering based on matching and averaging non-local neighbourhoods.

The spatial-spectral classification algorithm may involve an input base such as the pixel-wise classification representation and a guide such as the one-band representation of the hyperspectral cube produced by dimension-reducing algorithm. The spatial-spectral classification algorithm may compute the nearest neighbours in a feature space which may include both pixel value (classification) and spatial coordinates (reduced dimension map).

An unsupervised segmentation map may be generated by the clustering algorithm. The input of the unsupervised algorithm may be the hyperspectral cube with the complete pre-processing applied and the output may be a segmentation map that may comprise, for instance, 24 different clusters. In the segmentation map each pixel may be grouped into homogeneous region based on their spectral similarity (predetermined spectral features).

The cluster-wise classification map of the hyperspectral image may be generated by integrating together the spatial-spectral supervised classification map and the unsupervised segmentation map. In other examples, the integration may merge the classification map from supervised classifier algorithm and the unsupervised segmentation map.

The cluster-wise classification map may be generated by applying a majority voting technique. For each cluster found by the clustering algorithm, all pixels may be assigned to the most frequent classification in each cluster in the pixel-wise classification map.

The output data of each algorithm as cited herein may be represented as a map or any other alternative visualization of such output data. The optical device 2 may be configured to display the visualization of any output data generated as cited earlier.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow. If reference signs related to drawings are placed in parentheses in a claim, they are solely for attempting to increase the intelligibility of the claim, and shall not be construed as limiting the scope of the claim.

Further, although the examples described with reference to the drawings comprise computing apparatus/systems and processes performed in computing apparatus/systems, the invention also extends to computer programs, particularly computer programs on or in a carrier, adapted for putting the system into practice.

The invention claimed is:

1. A method of non-invasive detection of tumor and/or healthy tissue using hyperspectral imaging, the method comprising:
   determining a pixel-wise classification of a hyperspectral image obtained from a target tissue by implementing a machine learning approach fed with hyperspectral data of at least one pixel;
   performing a segmentation of the hyperspectral image by grouping pixels into at least one cluster based on the hyperspectral data of each pixel;
   assigning the same classification to all the pixels belonging to the same cluster, so that each cluster is associated with a certain classification; and
   performing a pre-processing of the hyperspectral data, prior to at least one of determining the pixel-wise classification, performing the segmentation, or assigning the same classification.

2. The method according to claim 1, wherein the method further comprises:
   performing a spatial homogenization of the pixel-wise classification, prior to assigning the same classification for all the pixels belonging to the same cluster.

3. The method according to claim 2, wherein the method further comprises:
   generating a spatially homogenized pixel-wise classification map of the hyperspectral image, after performing a spatial homogenization of the pixel-wise classification.

4. The method according to claim 2, wherein the spatial homogenization of the pixel-wise classification comprises:
   performing a dimensionality reduction of the hyperspectral data of each pixel;
   implementing a filtering approach fed with pixel-wise classification data and dimensionally-reduced hyperspectral data, the filtering approach assigning to a pixel the most common classification among its pixel-neighbours.

5. The method according to claim 1, wherein the method further comprises:
   generating a pixel-wise classification map of the hyperspectral image, after determining the pixel-wise classification.

6. The method according to claim 1, wherein the method further comprises:
   generating a segmentation map of the hyperspectral image, after performing the segmentation of the hyperspectral image.

7. The method according to claim 1, wherein the method further comprises:
   generating a cluster-wise classification map of the hyperspectral image, after assigning the same classification to all the pixels belonging to the same cluster.

8. The method according to claim 7, wherein the method further comprises:
   assigning in the cluster-wise classification map different chromatic properties to clusters with different classifications to each other, predefined chromatic properties being related to each classification.

9. The method according to claim 8, wherein the method further comprises:
   degrading chromatic properties of a cluster depending on the probability of the assigned classification.

10. The method according to claim 8, wherein the method further comprises:
    mixing different chromatic properties related to different classifications in the same cluster, taking into account the percentage of the probability of different classifications in the cluster.

11. The method according to claim 1, wherein the classification comprises at least one of the following classes: tumor tissue, healthy tissue, hypervascularized tissue, blood vessel, background element, primary tumor tissue and metastatic tumor tissue.

12. The method according to claim 1, wherein a classification is assigned to the cluster corresponding to the most frequent pixel classification in each cluster.

13. The method according to claim 1, wherein the pre-processing of the hyperspectral data comprises at least one of the following: image calibration, noise filtering and noise removing, band averaging and normalization.

14. The method according to claim 13, wherein the image calibration comprises correcting variations in the spectral signature of each pixel caused by non-uniform illumination over a surface of the target tissue.

15. The method according to claim 13, wherein the band averaging comprises removing at least one band of the hyperspectral image, the removed band being correlated with another consecutive band.

16. The method according to claim 13, wherein the normalization comprises homogenizing the amplitude of each pixel without modifying the shape of its spectral signature.

17. A hyperspectral imaging apparatus comprising:
an optical device configured to display a visible image of a target tissue;
a camera configured to obtain hyperspectral images of the target tissue;
a processing platform in data communication with the camera and the optical device;
the optical device being also configured to display information obtained from processed hyperspectral images;
the processing platform being configured to implement a method of non-invasive detection of tumor and/or healthy tissue using hyperspectral imaging, the method comprising:
determining a pixel-wise classification of a hyperspectral image obtained from a target tissue by implementing a machine learning approach fed with hyperspectral data of at least one pixel;
performing a segmentation of the hyperspectral image by grouping pixels into at least one cluster based on the hyperspectral data of each pixel;
assigning the same classification to all the pixels belonging to the same cluster, so that each cluster is associated with a certain classification; and
performing a pre-processing of the hyperspectral data, prior to at least one of determining the pixel-wise classification, performing the segmentation, or assigning the same classification.

18. The hyperspectral imaging apparatus according to claim 17, wherein the optical device comprises a surgical microscope; the surgical microscope comprising one eyepiece configured to display the visible image of the target tissue and another eyepiece configured to display the information obtained from processed hyperspectral images.

19. A computing device comprising a memory and a processor, embodying instructions stored in the memory and executable by the processor, the instructions comprising functionality to execute a method of non-invasive detection of tumor and/or healthy tissue using hyperspectral imaging of non-invasive detection of tumor and/or healthy tissue using hyperspectral imaging, the method comprising:
determining a pixel-wise classification of a hyperspectral image obtained from a target tissue by implementing a machine learning approach fed with hyperspectral data of at least one pixel;
performing a segmentation of the hyperspectral image by grouping pixels into at least one cluster based on the hyperspectral data of each pixel;
assigning the same classification to all the pixels belonging to the same cluster, so that each cluster is associated with a certain classification; and
performing a pre-processing of the hyperspectral data, prior to at least one of determining the pixel-wise classification, performing the segmentation, or assigning the same classification.

* * * * *